(12) United States Patent
Akopov et al.

(10) Patent No.: US 7,097,656 B1
(45) Date of Patent: Aug. 29, 2006

(54) DEVICE FOR THE THERAPEUTIC AND COSMETIC PHOTO-PROCESSING OF BIOLOGICAL TISSUE AND METHOD FOR USING THE SAME

(75) Inventors: Leonid Ivanovich Akopov, St. Petersburg (RU); Sergei Borisovich Birjuchinsky, St. Petersburg (RU); Mikhail Vladimirovich Inochkin, St. Petersburg (RU); Andrei Vyacheslavovich Belikov, St. Petersburg (RU)

(73) Assignee: LS Private Joint-Stock Company, St. Petersburg (RU)

( * ) Notice: Subject to any disclaimer, the term of this patent is extended or adjusted under 35 U.S.C. 154(b) by 0 days.

(21) Appl. No.: 09/719,497

(22) PCT Filed: Mar. 17, 2000

(86) PCT No.: PCT/RU00/00088

§ 371 (c)(1),
(2), (4) Date: Aug. 9, 2001

(87) PCT Pub. No.: WO00/54649

PCT Pub. Date: Sep. 21, 2000

(30) Foreign Application Priority Data

Mar. 18, 1999 (RU) ................................... 99105549

(51) Int. Cl.
*A61B 18/18* (2006.01)
(52) U.S. Cl. ................................ 607/90; 606/9; 606/10
(58) Field of Classification Search .............. 606/9–13; 607/88–93
See application file for complete search history.

(56) References Cited

U.S. PATENT DOCUMENTS

| 3,597,652 | A | * | 8/1971 | Gates, Jr. ..................... 315/205 |
| 5,320,618 | A | * | 6/1994 | Gustafsson ..................... 606/9 |
| 5,620,478 | A | * | 4/1997 | Eckhouse ....................... 606/9 |
| 5,759,200 | A | | 6/1998 | Azar ........................... 607/89 |
| 5,838,016 | A | * | 11/1998 | Johnson .................. 250/504 R |
| 5,859,503 | A | * | 1/1999 | Potratz ....................... 315/291 |
| 5,885,274 | A | | 3/1999 | Fullmer et al. ................. 606/9 |
| 5,968,034 | A | | 10/1999 | Fullmer et al. ................. 606/9 |
| 6,174,325 | B1 | * | 1/2001 | Eckhouse ..................... 607/88 |
| 6,283,956 | B1 | * | 9/2001 | McDaniel ....................... 606/9 |
| 6,413,253 | B1 | * | 7/2002 | Koop et al. ..................... 606/9 |
| 6,709,446 | B1 | * | 3/2004 | Lundahl et al. ............... 607/88 |

* cited by examiner

*Primary Examiner*—David M. Shay
(74) *Attorney, Agent, or Firm*—Thomas J. Engellenner; Deborah A. Miller; Nutter McClennen & Fish LLP

(57) ABSTRACT

The present invention relates to a method and an apparatus for permanently or temporarily removing human hair, for miniaturizing the same or for changing the color thereof. This apparatus can also be used for coagulating blood vessels, veins or a selective injury of the derma collagen in order to regenerate the same. This apparatus uses one or more incandescent lamps (4) in which the radiation spectrum (34) can be modulated in order to heat slowly and efficiently the derma (17) and in order to heat locally the hair follicles (35). This apparatus also includes an optical system that converts the blue-green portion of the spectrum of the incandescent lamps (4) into a red region of the spectrum, that provides a highly efficient concentration of converted radiation from the incandescent filament (37) of the lamps (4) on the area of biological tissues to be treated, and that ensures a repeated recirculation towards the skin (17) of the radiation scattered by the same.

23 Claims, 10 Drawing Sheets

DEVICE FOR THE THERAPEUTIC AND COSMETIC PHOTO-PROCESSING OF BIOLOGICAL TISSUE AND METHOD FOR USING THE SAME

TECHNICAL FIELD

The invention is classified with medical equipment and may be employed in dermatology for permanent or temporary removal of human hair, miniaturization of same, or alteration of color, and also for coagulation of blood vessels and selective destruction of collagen and subcutaneous fat.

PRIOR ART

The prior art knows devices for photo processing of biological tissues, whose operation is based on the selective heating of the desired area of biological tissue (skin, blood vessel, or hair follicle). These devices employ lasers or arc lamps as radiation sources.

For selective heating, lasers are the principal light sources. This is because a laser provides the best spectral selectivity. In addition, a laser enables production of any pulse duration, right down to several femtoseconds, and thereby affords selective heating of biological structures of all sizes. Laser radiation is easily focused in a small space. This enables achievement of the desired energy density level, and also affords high efficiency transmission via optical fiber to the operational field. At the same time, a laser is the most expensive light source, and is highly hazardous primarily to the user's eyesight.

For several applications, the capabilities of selective laser heating are unnecessary and may be effected by noncoherent sources such as lamps. In such cases, spectral selection is accomplished using an absorbent or fluorescent filter. U.S. Pat. No. 3,327,712 claims the use of an arc lamp with a filter in the 300–600 nm range and delivery of light via a fiber bundle for tissue coagulation, while U.S. Pat. No. 4,298,005 claims a device containing an arc lamp, a reflector, and a spectral filter in the 320–450 nm range for cosmetological applications; this device requires no fiber delivery of the radiation.

U.S. Pat. No. 5,320,618 describes a device which employs a fluorescent filter for selection of radiation from an arc lamp. The fluorescent filter absorbs the energy of the short-wave part of the lamp's spectrum, which does not affect the target and reemits it in the long-wave region, where the target is highly absorptive. U.S. Pat. No. 3,693,623 claims the first use of an arc lamp with a green filter and delivery of the radiation by optical fiber to remove a single hair by coagulating blood vessels in the papilla.

The common deficiency of the aforementioned patents lies in the fact that the devices specified therein contain arc lamps, which are generally less expensive and simpler than lasers, but require high-voltage heavy-current power supplies and cannot be used under home conditions or in cosmetology salons. In addition, devices based on arc lamps have very low efficiency. This is because their electricity to light conversion efficiency does not exceed 60%, while the power density on the outer surface of the plasma column is small due to the low "blackness" coefficient, limiting the maximum flux incident on the skin surface.

To create the least expensive photoepilators and photocosmetic devices, the most suitable light source at present is an incandescent lamp. An incandescent lamp can be powered by low-voltage sources safe for humans, and an incandescent lamp's electricity to light conversion efficiency is higher than that of an arc lamp (85% vs. 60%). An incandescent lamp's spectral efficiency is lower for the blue and green bands than that of an arc lamp due to limitations on filament temperature (<3800 K), but in the range of wavelengths in which hair is destroyed most efficiently (above 600 nm), its spectral efficiency is as good as that of an arc lamp with the same color temperature. The energy density on the surface of an incandescent filament is higher than that on the surface of a plasma column, which enables higher energy density to be achieved on the skin surface. Unlike an arc lamp, an incandescent lamp cannot efficiently emit pulses shorter than 50 ms, which is usually required for selective heating of the hair shaft or papilla, especially for fine hairs or the fine layer of dermis, subcutaneous fat, or blood vessels. For this reason, the development of an inexpensive and safe device for removing hair based on an incandescent lamp requires additional techniques for increasing the efficiency of action, which is the subject of this invention.

The device most similar to the claimed device, and the one selected as a prototype, is a device for coagulating blood vessels (U.S. Pat. No. 4,539,987, published Sep. 10, 1985).

Said device contains a source of electromagnetic radiation in the form of an incandescent lamp, a reflector to concentrate the radiation onto the area of biological tissue to be processed, and a transparent crystalline dielectric is placed between the incandescent lamp and the area of biological tissue to be processed and in contact with the area of biological tissue to be processed. This crystalline element, connected to a cooling system or heat sink, is designed to remove heat from the surface layer of the skin. An absorbent filter that passes radiation in the 600–1400 nm range may be placed between the lamp and the transparent dielectric. The device employs an incandescent lamp with an electric power of over 15 W, and develops a power density on the surface of the biological tissue to be processed exceeding 10 W/cm². The power density recommended in said patent is 150 W/cm², for which said device employs an incandescent lamp with a maximum electric power on the order of 400 W, operating in normal continuous mode with an exposure time of about two seconds. Coagulation of blood vessels is accomplished mainly through absorption of the lamp's radiation by water contained in the skin.

The deficiency of said device is its unsuitability for effective local heating of hair or fine blood vessels, fine layer of dermis, or subcutaneous fat. In fact, as shown by U.S. Pat. No. 5,735,844, published Apr. 7, 1998, destroying hair requires radiation with a wavelength of 600–1100 nm, an energy density no less than J/cm², and a pulse duration of 1–20 ms. Thus, the power density in this band must be at least 500 W/cm², which is considerably more than can be achieved using an incandescent lamp with a maximum electric power of 400 W in continuous operation, with an illuminated area of 25 mm in diameter on the surface of the biological tissue. We note that the nominal power of 400 W is the practical limit for miniature halogen lamps whose emissions can be concentrated in a small area (diameter 10–25 mm). Under these conditions, the light power in the 600–1400 nm spectral region on the surface of the biological tissue will not exceed 150 W (total light efficiency 80%, illuminator efficiency 80%, proportion of light in the 600–1400 nm band 60%; 0.8×0.8×0.6=0.4), and the power density will not exceed 40 W/cm², which again is considerably less than the required 500 W/cm². By reversing the calculation, we can easily ascertain that the required lamp power must be over 6 kW.

The most similar method to the claimed method of using the claimed device, and the one adopted as a prototype, is the method of removing hair specified in the aforementioned U.S. Pat. No. 5,735,844, published Apr. 7, 1998. This method employs short light pulses from 2 to 100 ms in length at a rate of 1 Hz and a wavelength in the 680–1200 nm band in combination with cooling of the epidermis. The essence of the prototype lies in the fact that melanin, which is contained primarily in the cell matrix of the hair follicle and in the hair shaft, is more absorptive in the specified frequency band than all other components of the skin. This enables selective heating of the hair follicle and destruction of its organs responsible for hair growth—the cell matrix in the papillary region and stem cells in the hair shaft region. Since melanin also occurs at the boundary between the dermis and epidermis, destroying the follicle can simultaneously damage the "epidermis, for example producing exfoliation. To prevent damage to the epidermis, said method employs cooling of the epidermis before and during light exposure. The hair removal method described in said patent is designed to process several hair follicles simultaneously with a single light pulse. The energy density of the optical pulses lies between 10 and 300 J/cm$^2$, and the method envisages the use of any pulsed sources of electromagnetic radiation, including lasers and noncoherent sources, with the aforementioned parameters.

The deficiency of the prototype method is the insufficient efficiency of its use of electromagnetic energy during processing due to suboptimal action of optical pulses with high energy density on biological tissue.

DISCLOSURE

The objective that the claimed invention aims to achieve is to reduce the device's cost while simultaneously increasing the efficiency and safety of hair follicle damage for permanent destruction or growth retardation, miniaturization or bleaching of hair, and coagulation of blood vessels and selective destruction of collagen in the skin and subcutaneous fat.

The stated objective is accomplished by achieving a technical result consisting in the optimal use of the properties of the biological tissue to be processed, consisting in the alteration of its state depending on the time, energy, and spectrum of incident radiation.

The aforementioned technical result is achieved in the claimed device by connecting an incandescent lamp, which is a source of electromagnetic radiation, to a power supply via a modulator. Said modulator contains a device for measuring the resistance of the lamp's incandescent filament and a power regulator, which ensure optimal biological tissue processing conditions. The inner surface of the reflector designed to concentrate the lamp's radiation onto the biological tissue is made reflective with the function of returning light reflected from the biological tissue being processed back to the biological tissue. This considerably increases the device's operational efficiency.

When the device is operating, a cooled dielectric prism consisting of a waveguide is in contact with the biological tissue being processed. In order to provide additional safety in processing, a metal plate is firmly joined to said dielectric prism, and said plate is also in contact with the biological tissue being processed and connected to a cooling system. During tissue processing, the device is moved so that the unexposed area of skin first contacts the metal plate, and then the dielectric.

The device also incorporates a spectral filter that absorbs radiation harmful to biological tissue, which together with the dielectric element forms an optical waveguide. This, in combination with the reflector's spherical inner surface and conical side surface, returns radiation reflected from the biological tissue back to the biological tissue.

Additionally, the reflector's interior may be equipped with an air cooling system.

In addition to the separate spectral filter, the bulb of the incandescent lamp and the reflective coating of the reflector's inner surface may be made to function as a fluorescent spectral converter.

The home version of the claimed device intended, for example, for removing hair under home conditions, may be made as "nippers" that grasp a fragment of skin containing a hair follicle in order to concentrate the radiation on it when the nippers are closed. The professional version of the claimed device may be made using several miniature lamps with power supply voltage below 40 W. The home version of the claimed device may contain one miniature lamp with a power supply voltage of up to 40 W.

Methods of using the claimed device to process various biological tissues differ in the action time, spectral band, and exposure time. The surface to be processed is first cooled, and then exposed in two phases. The exceptions are the destruction of dermal collagen aimed at stimulating regeneration and the destruction of subcutaneous fat.

The claimed device employs incandescent lamps and a current or voltage modulator that alters the lamp's emission spectrum over time so that at the beginning of light's action on the skin (phase one, preheating), the radiation peak is concentrated in the near-IR band, while at the end of action, it shifts to the red region (phase two, destruction). In phase one, the dermis is heated by absorption of radiation by water contained in the dermis to a temperature of 45–55° C., below its denaturing point. In phase two, when the peak of the emission spectrum shifts into the red part of the spectrum, the hair components containing melanin—the cell matrix and hair shaft and the adjacent papilla and stem cells—are selectively heated. Since phase 1 raises their initial temperature 9–15° C. above normal for the skin, the selective heating and destruction in phase 2 requires 30–40% less energy than heating without phase 1. To protect the epidermis from damage, contact cooling is used: the temperature of the epidermis can be measured, and when the skin reaches the specified temperature level in phase 1, heating can be terminated, and the energy of radiation in phase two is set at a safe level.

The distinguishing feature of phase two lies in the fact that the lamp power in this phase considerably exceeds the nominal value, but due to lamp preheating in phase one and the brevity of phase two, this does not destroy the lamp's incandescent filament.

The emission of one or more incandescent lamps, as in the prototype, is directed using a reflector to the area of skin being processed. Unlike in the prototype, this reflector, in combination with a waveguide, is built so that it returns radiation reflected from biological tissue back to the biological tissue, thereby increasing the efficiency of use of the lamp's power. The device's efficiency is further increased by the use of a fluorescent converter of ultraviolet, blue, and green radiant energy to the yellow-red part of the spectrum.

BRIEF DESCRIPTION OF DRAWINGS AND FIGURES

The essence of the invention is clarified by figures.

The diagrams and operating modes described below for the claimed device do not exhaust all possible options for embodiment of this invention. The device can be used widely for thermal action on various skin components using incandescent lamps. The use of this device is not limited to photoepilation or photomodification of hair; it may be used for action on large blood vessels, leg veins for purposes of treatment, on dermal collagen for purposes of regeneration, photobiostimulation, etc.

BEST EMBODIMENT OF THE INVENTION

Figure 1:
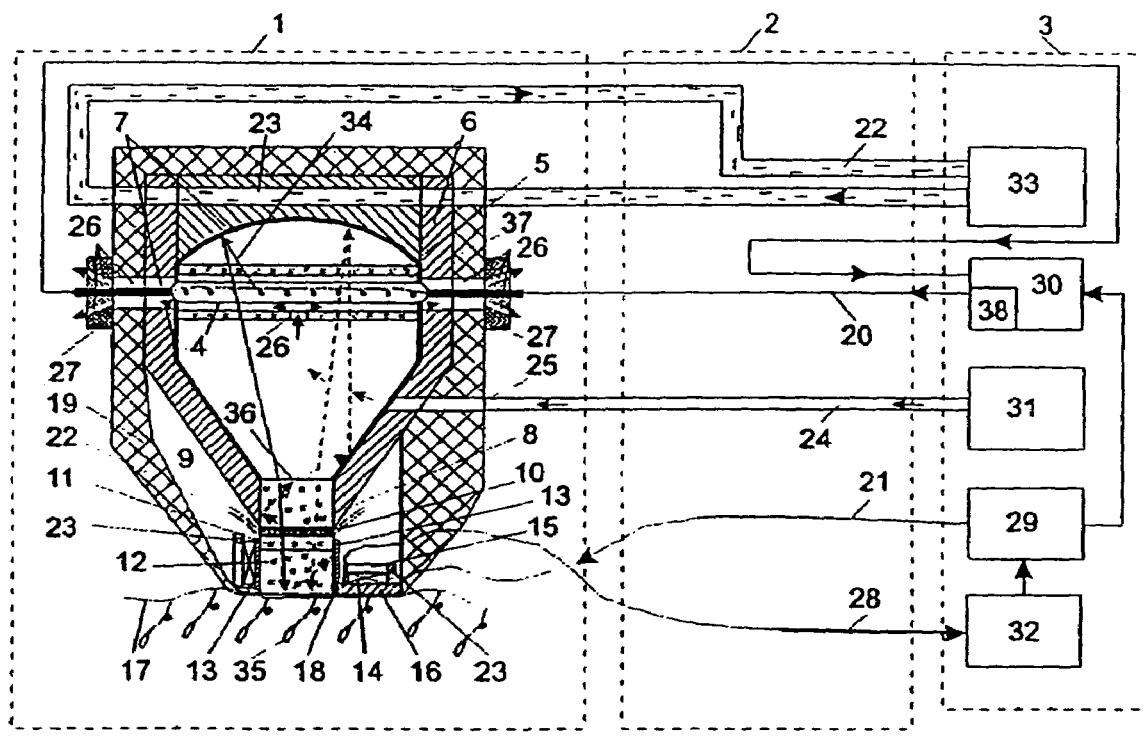
FIG. 1 shows a block diagram of the device and a cross section of its tip.

The device (FIG. 1) consists of tip 1, flexible wire and tube bundle 2, and power and control unit 3. Tip 1 consists of incandescent halogen lamp 4, which is placed in glass or dielectric crystal tube 5, reflector 6 made of metal or optical material whose inner surface has highly reflective coating 7, waveguide filter 8, consisting of a sandwich structure: fluorescent converter 9, nonfreezing coolant fluid 10, and optical thermal insulator 11; prism 12 of highly heat-conductive transparent dielectric material and fixed in metal mount 13, which is connected via thermoelectric elements 14 (for example, Peltier elements) to water-or air-cooled thermal radiators 15. The sandwich structure of filter 8 and dielectric prism 12 together form an optical waveguide. Mount 13 continues on one side as metal plate 16, which is connected to thermoelectric element 14. The lower surface of plate 16 and prism 12 are in contact with biological tissue 17 to be processed. Prism 12 is attached to heat sensor 18, which consists of a thermocouple, a thermistor, or a radiometer. These parts are mounted in heat-radiating body 19. Tip 1 is connected to power and control unit 3 by bundle 2, containing electric wires 20 for powering lamp 4 and wires 21 for powering thermoelectric elements 14. Liquid hoses 22 deliver coolant, which must circulate through holes 23 in reflector 6 and thermal radiator 15. Air line 24 delivers and passes compressed air through channel 25 to body 19 and reflector 6, and thence through holes 26 in tube 5, reflector 6, and electrode mounting assemblies 27. Wires 28 deliver signal from heat sensor 18. Power and control unit 3 consists of power supply 29, current, voltage, or power modulator 30, compressor 31, microprocessor 32, and cooling system 33 with liquid pump.

The device, using the case of hair removal for illustration, operates as follows: emissions 34 from lamp 4 pass directly or with the aid of reflector 6 through element 8, which blocks undesirable spectrum, and strikes skin 17 and acts on it through absorption by water. This radiation also acts on the target, for example, on hair follicle 35 through light absorption by melanin or on a blood vessel through light absorption by: blood components. It is known that after bulk scattering in skin; a large part of the light is backscattered (S. R. Utz et al. "Percutaneous Blood Laser Biostimulation. First Clinical Results." *Proc. SPIE*, 1992, vol. 1643, pp. 228–239). This effect is maximal in the red part of the spectrum, where skin absorption is minimal. The coefficient of reflection can reach 80% (V. G. Peters et al. *Phys. Med. Biol.* 35, 1990, pp. 1317–1334). If, for example, part of reflector 6 located above incandescent lamp 4 consists of part of a sphere, and the center of curvature of that sphere is located on facet 36 of filter a, which is closest to lamp 4, the emissions 34 diffusely reflected from skin 17 passing through the waveguide formed by elements a and 12 will exit through that facet. Then, striking the spherical reflective surface 7 of reflector 6, they are returned to said facet 36 and thence through the waveguide again to skin 17. In the claimed device, these emissions are sent back to reflective coating 7 of reflector 6 and returned again to skin 17. The gentle slope of the lateral inner surface 7 of reflector 6 ensures that even rays that have struck the lateral surface after leaving facet 36 fall on the spherical part.

The efficiency of re-reflection is very high because the inner surface 7 of reflector 6 is coated with a highly reflective material: Cu, Au, or Ag or a multilayer dielectric. The coefficient of reflection exceeds 90%. Moreover, the surface area of the incandescent filament 37 of lamp 4 is very small, the material of tube 5 and reflector 6 has very low absorption at the wavelengths of the light acting on skin 17. So each re-reflection of emissions into the skin returns $Rr^n$ part of the energy striking it, where R is the coefficient of reflection of the skin, r is the coefficient of reflection of the surface 7 of reflector 6, and n is the number of reflections. As a result of the multiple reflections, the illumination within the skin is increased by $$\frac{1}{1-(Rr^n)}.$$

For R=0.8, r=0.9, and n=2, the illumination is increased by as much as a factor of four. We should note that the best increase in illumination within the skin by photon recirculation is achieved with a spot size larger than 10 mm.

Figure 2:
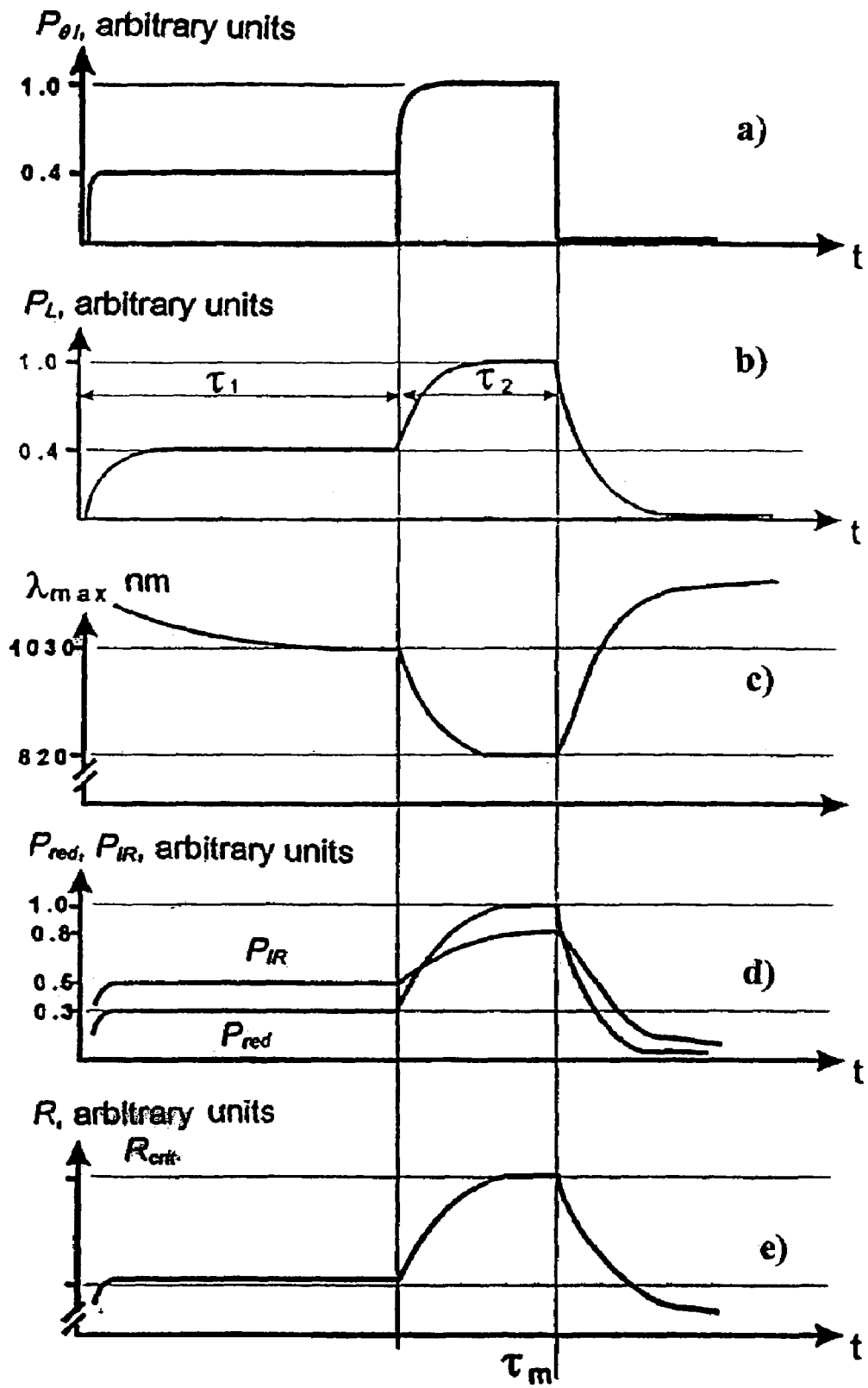
FIG. 2 shows the time variation of the lamp's power, peak radiation wavelength, proportion of the lamp's emissions in the infrared and red parts of the spectrum, and the lamp's resistance.

Let us consider the lamp heating regime using power supply 29 and modulator 30. The most favorable part of the lamp's spectrum for destroying hair follicle 35 is 600–1100 nm. In this region, the melanin has a fairly high absorption, while scattering is moderate, so that the light can penetrate the skin to a sufficient depth. Halogen lamps have peak temperatures of 3000–3600 K. At 3000 K, 5% of their emissions are concentrated in the λ<600 nm region, 34% are in the 600 nm <λ<1100 nm region, and 48% are in the 1100 nm<λ<2500, nm region. At 3500 K, these percentages are redistributed thus: 10% λ<600 nm, 42% 600 nm <λ<1100 nm, and 35% 1100 nm <λ<2500 nm. Thus, to maximize the efficiency of conversion of electrical energy to useful light energy, it is advantageous to boost the power and temperature of halogen lamp 4. However, this sharply reduces the lamp's service life, if it is used in normal continuous operation. The claimed invention employs electric modulator 30, enabling delivery of a short current or voltage pulse to lamp 4 that increases the power scattered by the lamp above nominal. Research performed by the authors with OSRAM lamp type ELC (Germany), which has a nominal power $P_{nom}$ of 250 W, has shown that a temperature of 2800 K corresponds to a power of 150 W at 9 A and 17 V. If the current is increased to 12.5 A over a time interval of 0.2 second, a power of 360 W will be scattered in the lamp, which is 1.45 times greater than nominal (FIG. 2a). The temperature will reach 3600 K, i.e., it will approach the maximum. Under conditions when the average filament temperature is on the order of 2800 K, but briefly (for 0.2 s) reaches a peak of 3600 K, lamp 4 can operate for a very long time without deterioration or failure. The lamp's power-time curve corresponds to the photoemission curve shown in FIG. 2b. The shape of the light pulse may differ from that of an electrical pulse due to the thermal inertia of incandescent filament 37. The thermal inertia depends on the diameter of incandescent filament 37. At the practical limit for the diameter of filament 37, 0.2 mm, the thermal inertia time is 0.04 s, and the minimum FWHM duration $t_2$ of the light pulse can reach 0.1 s. For a 250 W lamp, such a pulse can concentrate up to 50 J of light energy with a FWHM duration of 0.2 s. By regulating the current of lamp 4 with modulator 30, the emission spectrum of lamp 4 can also be tuned. In phase one, with a duration of $t_1$, the lamp current is below nominal, the temperature of filament 37 is 2800 K, and the emission peak lies in the IR part of the spectrum (1030 nm). In phase two, the temperature of filament 37 reaches 3600 K and the emission peak is retuned to the red (800 nm) region (FIG. 2c). The proportion of emissions lying in the 1100–2500 nm region, $P_{IR}$, and in the 600–1100 nm region, $P_{red}$, change correspondingly (FIG. 2d). Additionally, in order to automatically protect lamp 4 from damage, modulator 30 continuously monitors the lamp's resistance. When an above-nominal current pulse is delivered, the resistance of incandescent filament 37 increases, and at time $t_m$ (FIG. 2e), when the resistance reaches a critical value, modulator 30 automatically restricts the scattered power. For this purpose, modulator 30 contains resistometer 38 for incandescent filament 37 of lamp 4, connected to a current, voltage, or power regulator.

The method of processing various biological tissues using the claimed device is determined based on the degree of susceptibility of a given biological tissue to the irradiation parameters. In particular, the method of using the device to remove hair is determined by the properties of skin and hair bulb (see, for example, A. Waldman et al. "Laser Hair Removal: Theory and Clinical Experience." *Proc. SPIE*, 1998, Vol. 3245, pp. 318–321).

Calculations performed according to a mathematical model developed by the authors have shown that two phases of heating are needed: a long one (preheating) and a short one (heating and destruction). In addition, the photodestruction of a hair follicle requires first cooling the upper layer of skin (epidermis) and then beginning to irradiate the skin while continuing to cool.

In fact, in the spectral region from 1100 to 2500 nm, skin possesses strong absorption (water absorption) and weak scattering. In the 600–1100 nm band, melanin and blood hemoglobin are the primary absorbers. Thus, in phase one of the radiation's action on it, the skin is nonselectively heated through radiation absorption by water. In phase two, the skin's melanin-containing structures (epidermis, hair shaft, cell matrix of hair bulb) and hemoglobin (blood vessels, veins) are selectively heated. The role of phase one consists of preheating the target to be destroyed (hair bulb, blood vessel) from 30–36° C. to 45–55° C. (which is below the protein denaturing point). This is done in order to reduce the energy level required for phase-two heating. In phase two, the target to be destroyed (hair bulb, vessel) is heated by a short pulse to the protein denaturing point of 65–75° C.

Usually, the illumination peak is on or near the surface layer of the skin. This does not permit uniform heating of deeper layers of the skin. The inclusion of contact cooler 16 with subfreezing temperature maintained by a cooler in the form of thermoelectric elements 14 or thermal radiator 15 with circulating water reduces the temperature of the surface and subsurface layer and shifts the temperature peak in phase one deeper into the skin. Combining the coolant temperature and lamp power permits smooth control of the temperature profile within the skin. This effect can be used for selective destruction of collagen in order to stimulate its growth.

Figure 3:
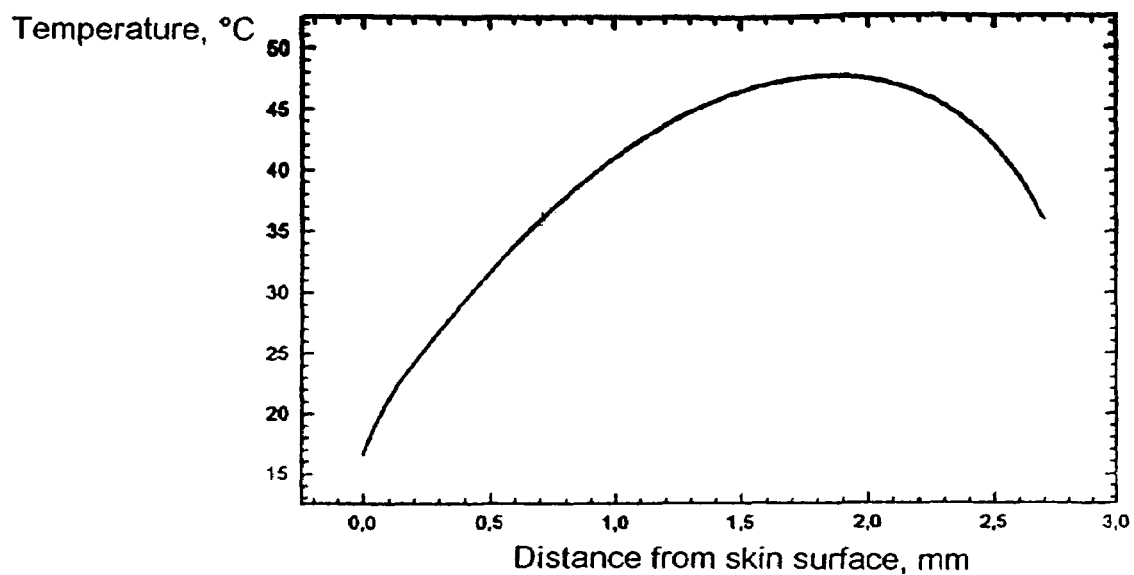
FIG. 3 shows the distribution of temperature within the skin at the completion of phase one, preheating.

FIG. 3 shows a typical temperature profile within the skin, calculated for the case of a contact cooler made of sapphire crystal at a temperature of −10° C. and a lamp with a nominal power of 250 W and a filament temperature of 3600 K through an illuminated section of skin 1.5×1.5 cm² and one second after the beginning of action (phase one). By the time this phase is complete, the use of contact cooler 16 has reduced the temperature of the basal membrane to 17° C. This enables protection of the epidermis from injury in phase two.

Figure 4:
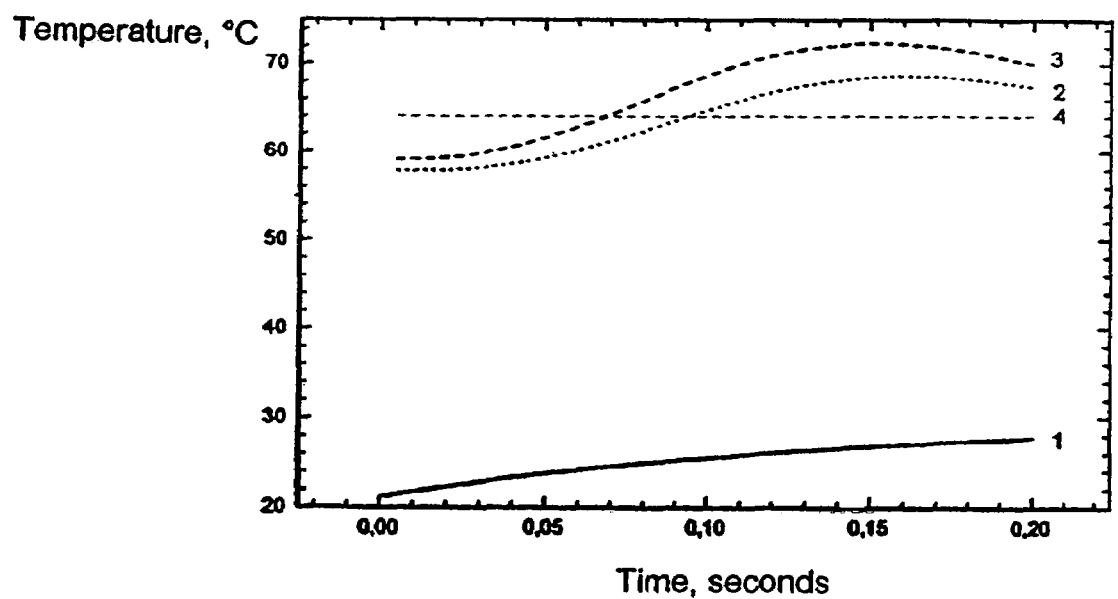
FIG. 4 illustrates the time relation of the temperature of the base layer, stem cells, and cell matrix of the hair follicle in phase two.

FIG. 4 shows time diagrams of the temperature (phase two) of the basal membrane (curve 1), stem cells (curve 2) and hair follicle cell matrix (curve 3). The horizontal line (4) corresponds to the protein denaturing point. The incandescent lamp's peak temperature is 3600 K, its peak power is 1.45 times nominal, the peak radiated power density in the 600–1100 nm spectral band is 81.6 W/cm², the spot size is 1.5×1.5 cm², and the duration of phase two is 0.2 s. Achieving the thermal destruction of hair bulb 35 requires the temperature in the area of the papillae and stem cells to reach the protein denaturing point, i.e., 65–75° C. Calculations based on models of the skin and hair bulb using data described in the literature (M. H. Niemz, *Laser-Tissue Interaction, Fundamentals and Application*, Springer, 1995) show that for the device design described above, the optimal method of hair follicle photodestruction is as follows: pre-cool the skin by contact with metal plate 16 and dielectric prism 12, then, while maintaining the contact and continuing to cool, heat the dermis with radiation in the 1100–2500 nm band with a peak at 1300–1400 nm and a density of 10–60 W/cm² and a duration of 0.1–100 s. In phase two, immediately following phase one, perform destruction in the hair follicle by radiation 0.05–10 s in duration in the 600–1200 nm band with a peak in the 600–1000 nm region and a power density of 80–800 W/cm².

The method of using the device to coagulate blood vessels is determined mainly by the optical properties of hemoglobin (see, for example, T. J. Pfefer et al. "Laser Treatment of Port-Wine Stains: Three-Dimensional Simulation Using a Biopsy-Defined Geometry in an Optical-Thermal Model." *Proc. SPIE*, 1998, vol. 3245, pp. 322–333). Just as in the case of the hair follicle, precooling is required, followed by irradiation in two phases with simultaneous cooling. Calculations show that in phase one 0.1–100 s in duration, irradiation is performed with radiation in the 500–2500 nm band with a maximum in the 700–1500 nm region and a power density of 1–50 W/cm². In phase two, to coagulate vessels or veins, the duration of action must be 0.05–5 s in the 400–1200 nm band with a peak in the 500–1100 nm region and a power density of 10–500 W/cm².

The specified device may also be used for selective destruction of dermal collagen in order to stimulate its growth and consequently improve the cosmetic properties of the skin (reduce wrinkling and increase elasticity) or to destroy subcutaneous fat. Calculations based on our model using literature data (A. Welch. *Optical-Thermal Response of Laser-Irradiated! Tissue*. Plenum Press, NY, 1996) have shown that the optimum conditions for selective destruction of collagen-using the specified device are as follows: cool the skin by contact with metal plate 16 and dielectric prism 12 and irradiate with light from incandescent lamps in the 600–2500 nm band for 0.1–1000 s with a power density of 0.1–500 W/cm². Under these conditions, the simultaneous surface cooling and bulk heating of the dermis or subcutaneous fat by radiation from the incandescent lamp shifts the temperature peak deep into the skin, destroying the collagen layer while preserving the epidermis. The depth of destruction is determined by the duration of heating and cooling. The lower the power and longer the cooling, the deeper the damaged area lies. The skin may be cooled during the use of the specified device as it is slid along the surface with thermal contact maintained. In that case, the new unirradiated section of skin first contacts metal plate 16 and is precooled, and then that section contacts prism 12 and is cooled while being irradiated.

The simplified (nipper) versions of the tip of the claimed device depicted in FIG. 5 are characterized by the fact that transparent dielectric 12 is split (divided into two halves along plane of symmetry 39) and made of material that absorbs radiation from lamp 4 harmful to the biological tissue being processed, i.e., it incorporates the functions of filter 8. Moreover, each half is fixed on movable elements, some parts of which perform the role of reflector 6 with the function of focusing the radiation from lamp 4 on the fragment of skin 17 fixed between the halves of transparent dielectric 12, for example, by an elementary clamp. The reflector halves are combined with handles 40, whose closure about axis 41 clamps skin 17. A device with such a tip is more convenient to use at home.

Figure 5A:
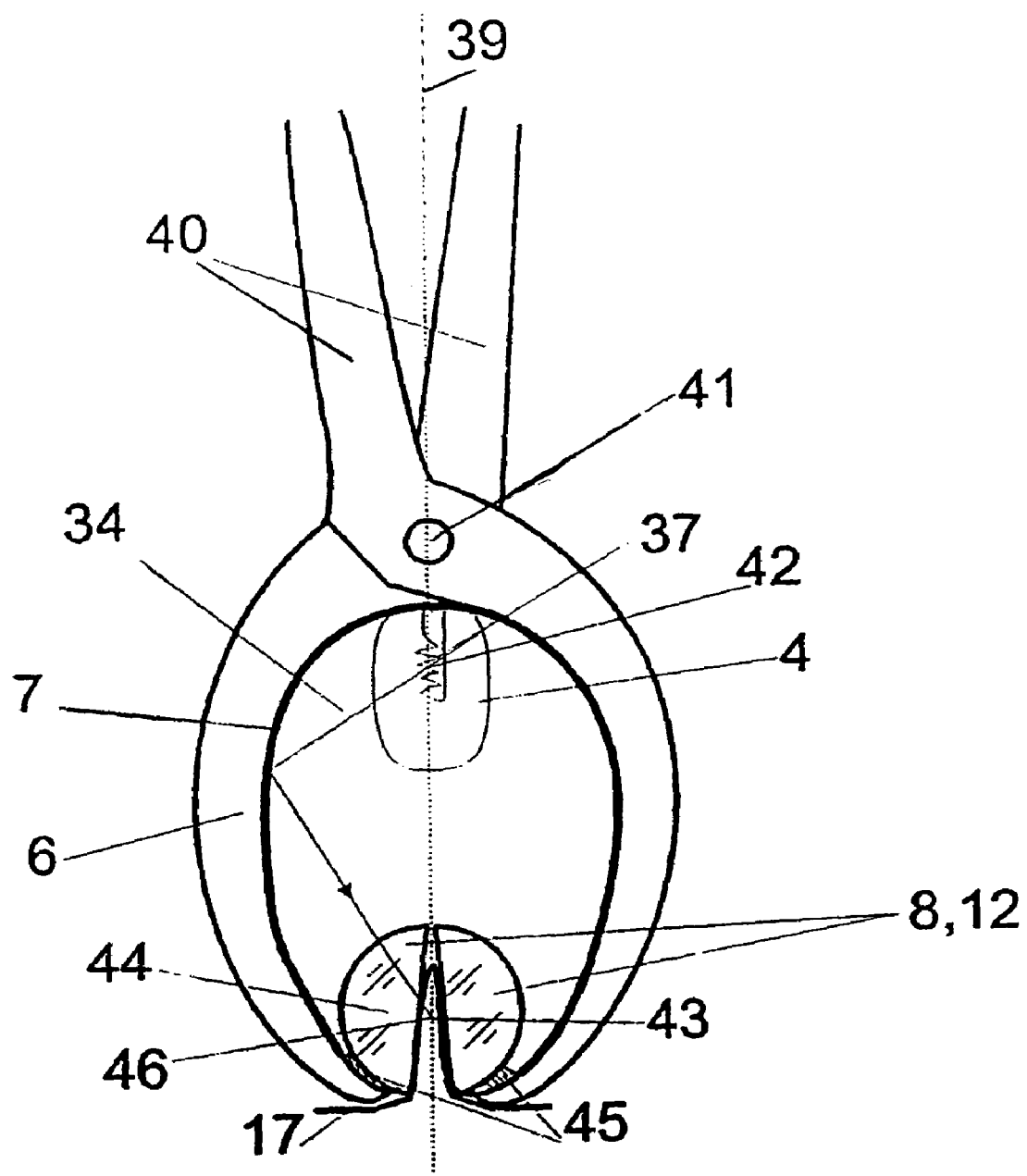
FIG. 5a shows the cross section of the tip of the simplified version of the device with low average power and made in the form of "nippers" with the inner surface of the reflector shaped as an ellipsoid of revolution and the coil of the incandescent filament oriented along the major axis of the ellipsoid.
Figure 5B:
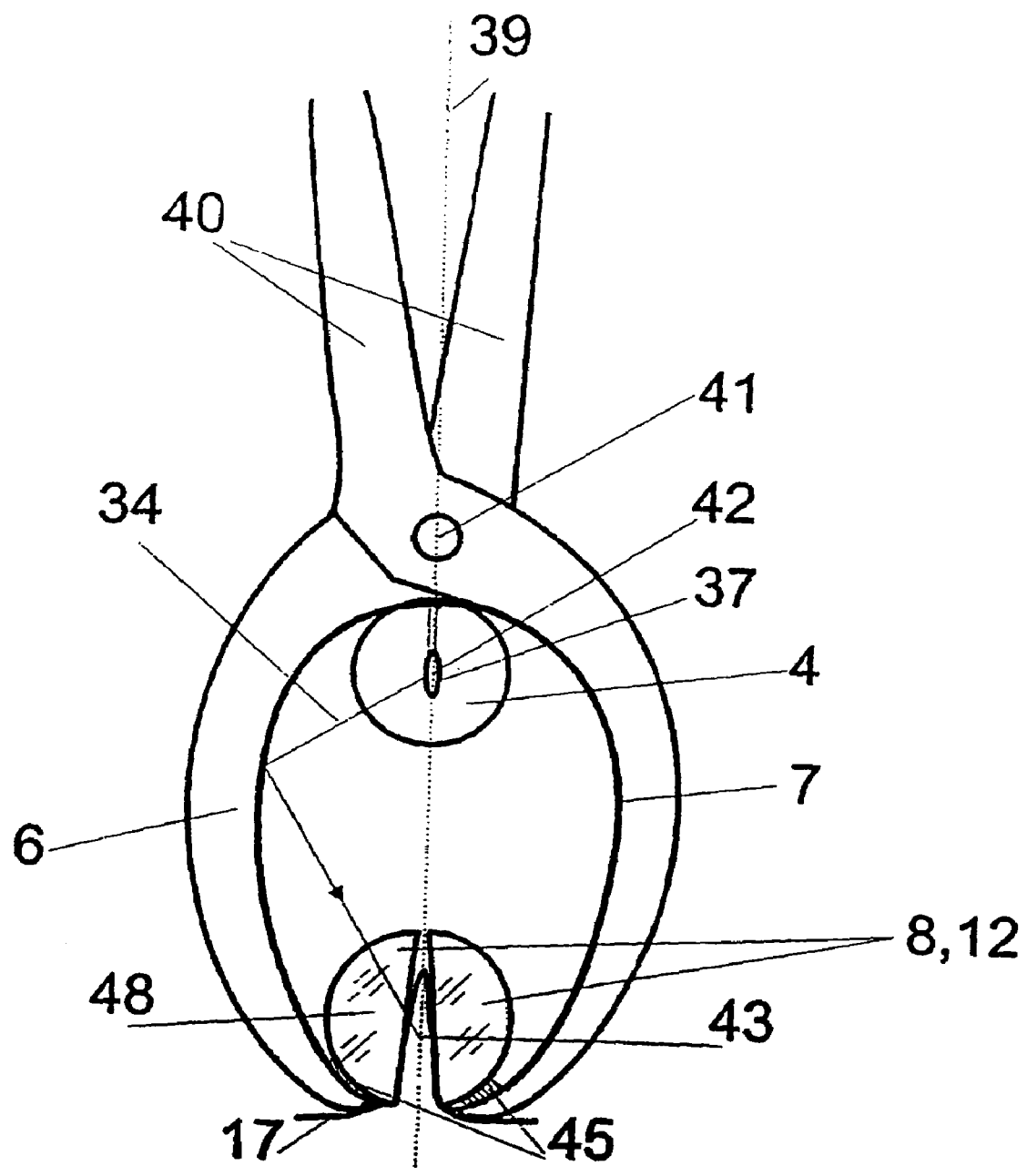
FIG. 5b shows the "nippers" with the inner surface of the reflector shaped as an elliptical cylinder, the coil of the incandescent filament oriented along the generatrix of the cylinder, and the dielectric element shaped as a cylinder.
Figure 5C:
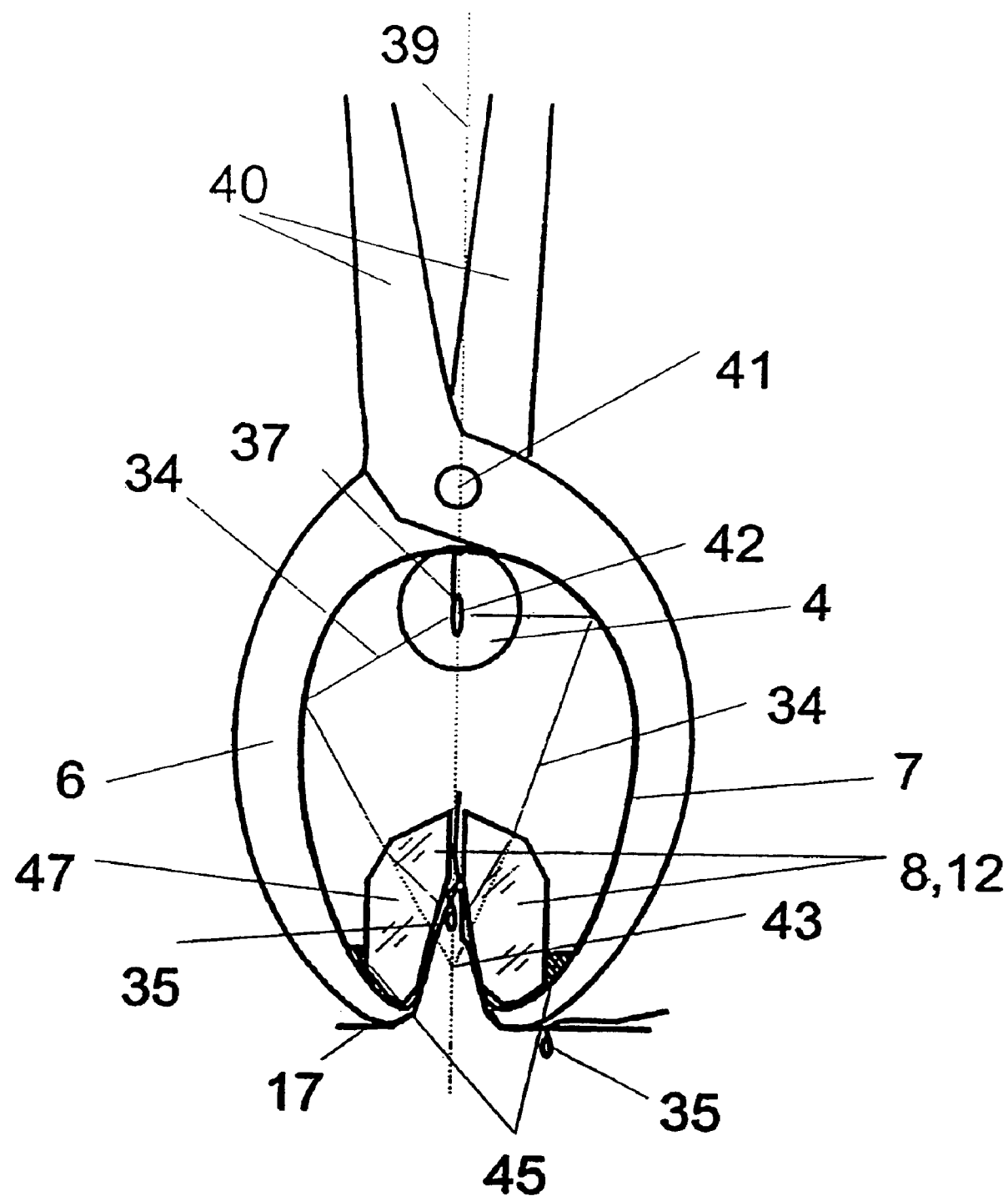
FIG. 5c shows the "nippers" with the inner surface of the reflector shaped as an elliptical cylinder, the coil of the incandescent filament oriented along the generatrix of the cylinder, and the dielectric element shaped as a prism.

As FIGS. 5a, 5b, and 5c show, the inner surface of the "nippers'" reflector in the closed position has an elliptical shape. If the coil of incandescent filament 37 is placed at one focus 42 of the ellipse, the radiation 34 emitted from said filament is concentrated after reflection from the elliptical surface at the second focus 43. The distortion of the path of rays 34 due to the presence of dielectric element 12 will be minimal if the rays emitted from one focus 42 and reflected from the inner surface of the ellipse strike that element normally. To this end, the cross section of dielectric element 12 must be round. A polygonal shape (easier to manufacture) is also possible; the number and orientation of the facets is selected to meet the criterion of concentrating the maximum proportion of the radiation at the second focus 43 of the ellipse.

FIG. 5a shows the "nippers" with the inner surface 7 of reflector 6 shaped as an ellipsoid of revolution and the coil of incandescent filament 37 oriented along the major axis 39 of the ellipsoid. In this case, radiation from incandescent filament 37 is emitted primarily perpendicular to said ellipsoid axis 39 and, after reflection from the inner surface 7 of reflector 6, strikes all sides of dielectric element 12, which is made in the form of sphere 44 and fixed using fixator 45, and is concentrated in the area of the second focus 43 of the ellipsoid, which coincides with the center 46 of sphere 44.

FIGS. 5b and 5c show the "nippers" with the inner surface 7 of reflector 6 shaped as an elliptical cylinder and the coil of incandescent filament 37 oriented along the generatrix of the cylinder. In this case, radiation from the incandescent filament is emitted primarily perpendicular to the generatrix of the cylinder and, after reflection from the inner surface 7 of reflector 6, is concentrated in the area of the second focus 43 of the ellipse. The shape of dielectric element 12 shown in the figure (prism 47 or cylinder 48) does not alter the direction of radiation 34.

Figure 6:
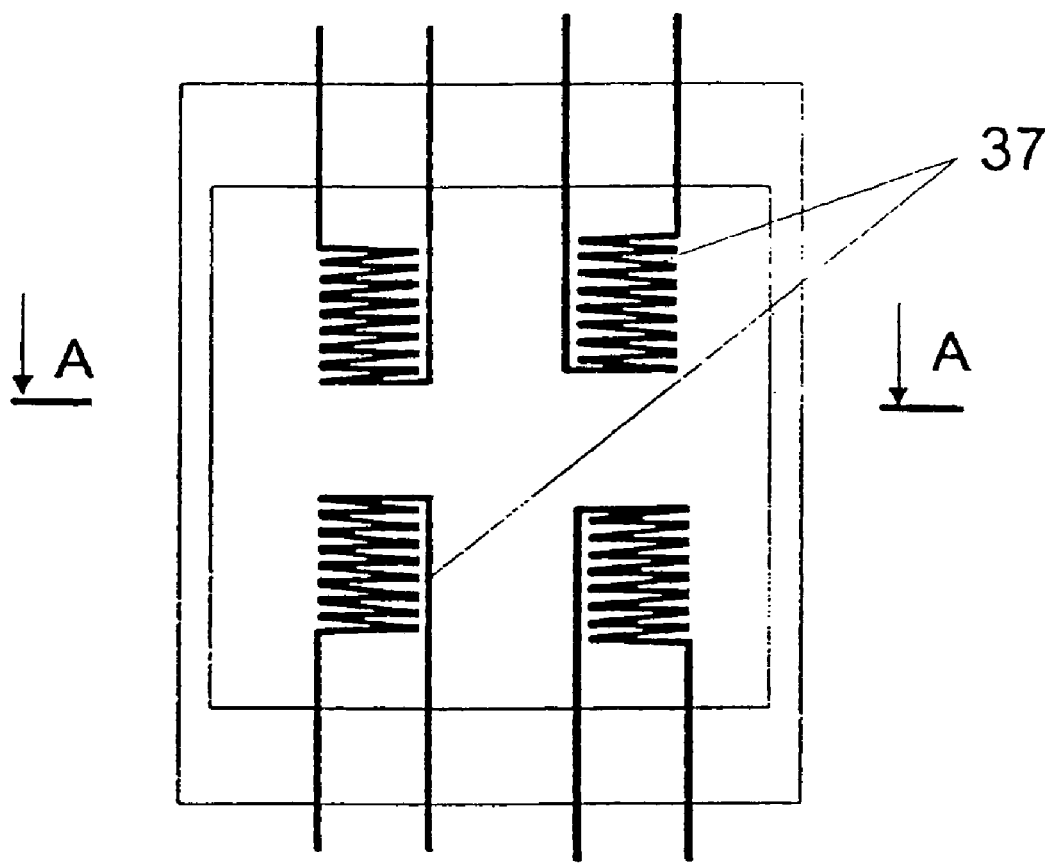
FIG. 6 shows the cross section of the device's lamp containing several flat coil.
Figure 6:
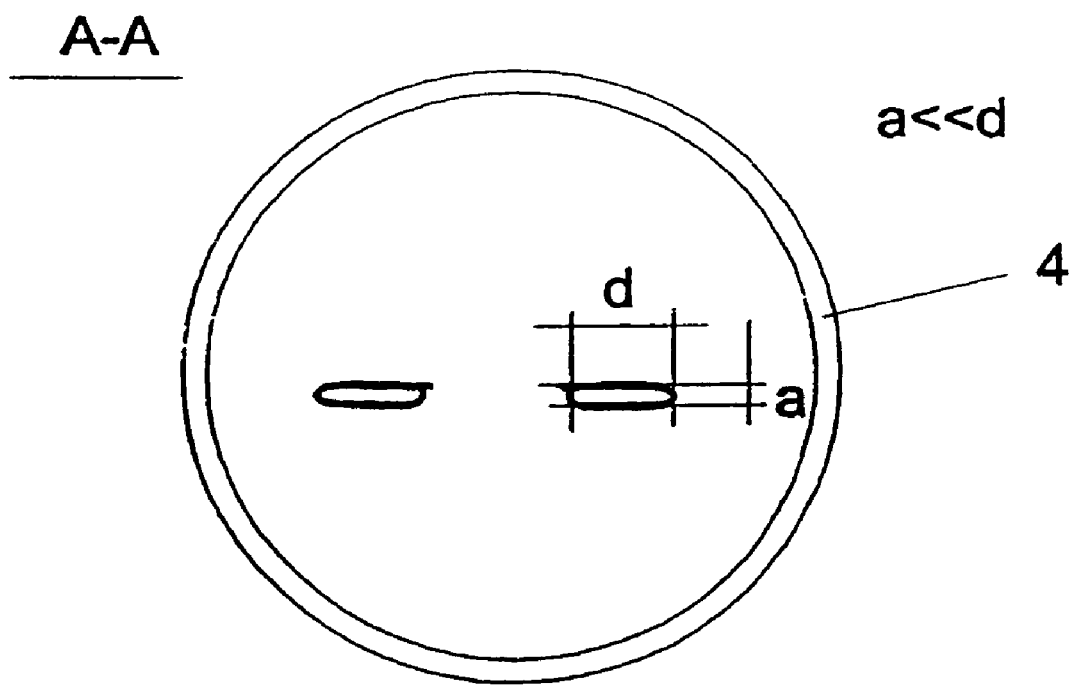

FIG. 6 depicts the version of cylindrical incandescent lamp 4 with four incandescent filaments 37 in a single bulb, designed for use in a cooled tip. If the incandescent filament in the lamps are made so that its geometric dimensions in a plane perpendicular to the illuminated surface of biological tissue 17 is much smaller than the filament's dimensions in other directions, its radiation will be emitted primarily parallel to that plane. This will reduce losses to mutual rescattering of radiation from one incandescent filament on the others and increase the device's overall efficiency. In principle, the placement of several incandescent filaments in a single bulb enables elimination of the tubes guiding the cooling air flow, reduces heat losses through gas and light losses on bulbs and air guide tubes, and improves the fabricability of lamps for this device through simplification of the current input design.

Figure 7A:
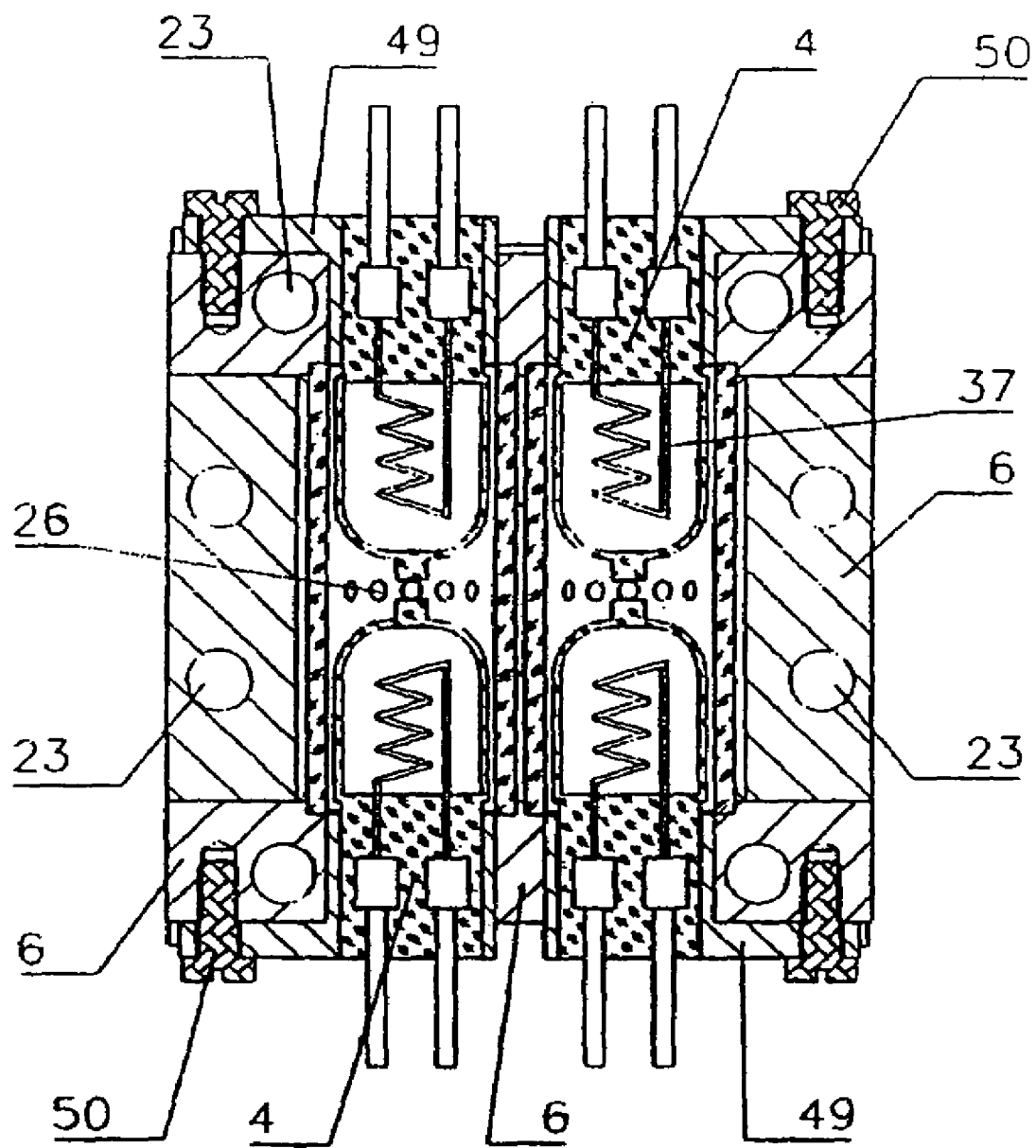
FIG. 7a depicts a cross section of a tip containing four lamps in the plane of the incandescent filaments of the fabricated tip.
Figure 7B:
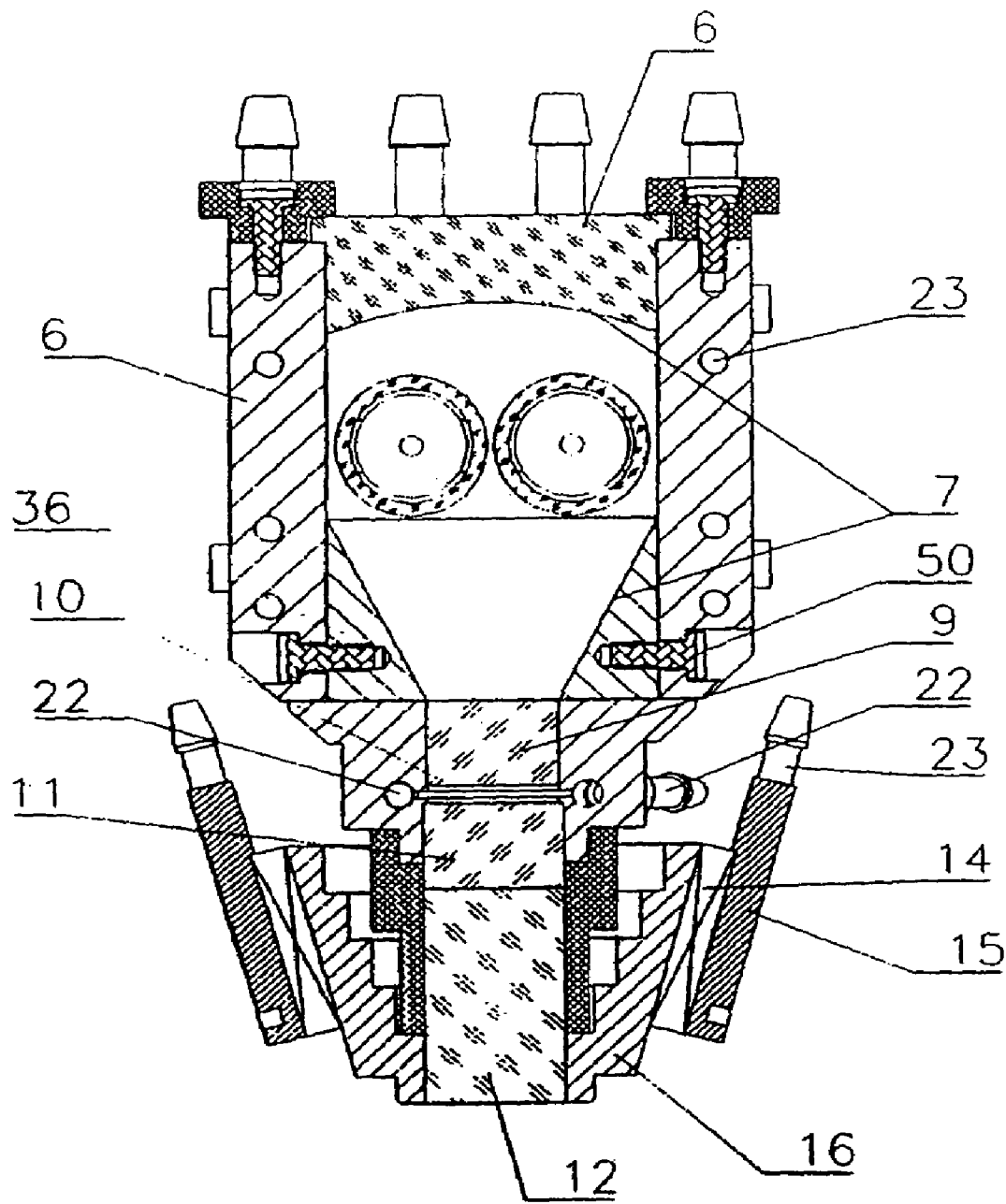
FIG. 7b depicts a cross section of a tip containing four lamps in the plane of the main optical axis of the spherical part of reflector 6.

FIG. 7a depicts the cross section in the plane of the incandescent filaments of the fabricated tip claimed hereunder, and FIG. 7b depicts the cross section in the plane of the main optical axis of the spherical part of reflector 6. Reflector 6 is a modular structure made of plates. Four halogen lamps are glued into bracket 49, which in turn is fixed to the plates of the reflector with screws 50. The experimental mockup employed four OS-RAM type ELS lamps. Radiation from lamp 4 passed through the walls of the bulb and quartz tube 5, directly or after reflection from the silvered walls of the aluminum alloy reflector, through a spectral filter consisting of ruby, a thin layer of water, and a quartz wafer onto sapphire dielectric element 12, and then struck the surface of the skin. In the experiment, the skin surface was cooled with a cooling system based on Peltier elements brand TV-17-0,1.

The cross section of the waveguide in contact with the skin was 15×15 mm. In the 650–1200 nm part of the spectrum, the power density on the skin surface in phase 1, which lasted 0.5–1 s, was 20 W/cm², and in phase two, which lasted 0.2 s, it was 85 W/cm².

Figure 8:
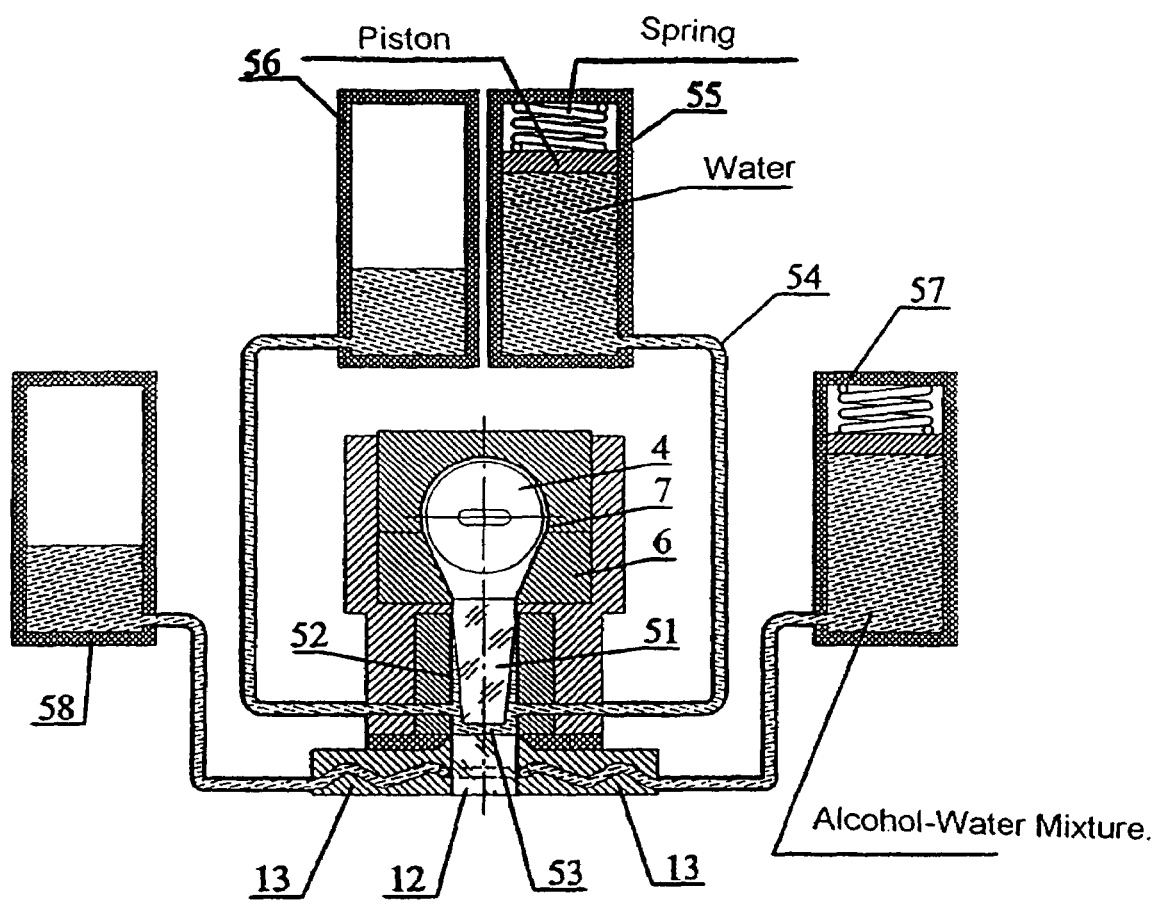
FIG. 8 depicts one embodiment of the invention in which the device has one halogen lamp that is oriented with its longest dimension horizontal relative to the surface of skin.

The embodiment of the device using one halogen lamp is shown in FIG. 8. In this device, lamp 4 is oriented with its longest dimension horizontal relative to the surface of skin 17. If the shape of the incandescent element is asymmetric, the lamp bulb is oriented horizontally relative to the skin surface so that the surface of coil 37 with the greatest area is facing the skin surface. In this case, the waveguide effect in the direction of propagation of the radiation from the lamp toward the skin is provided mainly by element 51 in the form of frustum of pyramid 51 with high index of refraction (no less than 1.76), and in the direction of propagation of radiation reflected from the skin it is provided mainly by reflective surface 52. The space between the surface of element 51 and surface 52 forms cell 53, connected with line 54 filled with meltwater at +1° C. from reservoir 55, which goes to discharge tank 56. Prism 12 is made of sapphire, fixed in metal mount 13, within which the design provides for flow of liquid at 0–5° C. formed by melting of solid multi component substance, for example frozen water-alcohol solution, contained in reservoir 57, which is connected to tank 58, where the liquid at 0–5° C. is collected. In this embodiment of the claimed device, power and control unit 3 may incorporate a feedback system consisting of an actuator and a sensor (not shown).

The shape of the reflective surface 7 of reflector 6 and its position in the immediate vicinity of lamp 4 is selected to minimize the length of the optical path between the emitting surface of the incandescent filament 37 of lamp 4 and the opposite surface of waveguide 51 and maximize light transmission. Waveguide 51 is most efficient due to the phenomenon of total internal reflection, and transmits light from surface 7 through a liquid filter and sapphire wafer to the skin surface. The liquid filter selectively absorbs the IR component of the lamp's emission, attenuating light in this part of the spectrum to the optimal level. The liquid filter is water formed by the melting of ice in reservoir 55 and flowing under low pressure to cell 53, the filter water heated by the IR light enters the meltwater collection tank via a line. Reservoir 55 and meltwater collection tank 56 are replaceable. Sapphire wafer 12 is cooled to a temperature on the order of 0–5° C. by the passage of liquid formed by the melting of a solid multicomponent (for example, frozen water-alcohol solution) in reservoir 57 via lines 59 within metal mount 13. Reservoir 56 and collection tank 58 for liquid at 0–5° C. are also replaceable. The melting of ice and solid multicomponent substance begins when reservoirs 55 and 57 from the refrigerator are placed in the device and is due to the influx of ambient heat at room temperature. The use of liquid at 0–5° C. is necessitated by the need for precooling, for example of the epidermis, to below 0° C. during contact with sapphire wafer 12 and metal mount 13 before, during, and after irradiation. Melting is the phase transition that enables most efficient storage of heat from the skin and liquid filter.

The lamp is electrically powered by a power supply that creates electric pulses of the requisite voltage, current, and duration. The power supply may be off-line, due to incorporation of a single-use or rechargeable electrolyte battery.

It must be noted that the processing procedure may be painful. To increase comfort and reduce injury, the device incorporates a feedback system. In the simplest version, it consists only of an actuator such as a push-button switch or pedal that terminates delivery of electricity at the patient's wish and can be controlled by the patient. Options are possible wherein the sensor that reports crossing of the pain threshold is a sensor that monitors pupil size (when the pain threshold is crossed, the pupil contracts sharply), the rate of blood flow (when the pain threshold is crossed, the rate of blood flow drops sharply), or the temperature of the surface being processed (when the pain threshold is crossed, the temperature reaches a certain value), and based on these signals the actuator alters the current passing through the lamp or terminates the delivery of electricity.

When this device is used, the cooling phase may occupy a considerable time interval, and the lamp does not emit until the epidermis reaches a temperature close to 0–5° C. as indicated by a signal received from the temperature sensor (thermocouple, thermistor, radiometric sensor, etc.).

If biological tissue with a fairly large surface area must be processed, several similar devices may be used simultaneously, with their outputs forming a matrix of emitters and coolers in contact with the skin.

The invention claimed is:

1. A device for therapeutic and cosmetological photoprocessing of biological tissue, comprising:
   an incandescent lamp for emitting electromagnetic radiation;
   a waveguide for directing the electromagnetic radiation toward biological tissue;
   a resistometer for measuring electrical resistance of the incandescent lamp; and
   a power modulator for adjusting power delivered to the incandescent lamp during use based on resistance measurements.

2. The device of claim 1, wherein the power modulator is configured to intermittently increase power to the incandescent lamp such that the power to the incandescent lamp exceeds the nominal power rating of the incandescent lamp.

3. The device of claim 2, wherein the power modulator is configured to decrease the power to the incandescent lamp when the electrical resistance of the incandescent lamp reaches a predetermined value.

4. The device of claim 1, wherein the incandescent lamp includes a halogen lamp.

5. The device of claim 1, wherein the incandescent lamp includes a filament oriented such that a dimension of the filament projected in a plane perpendicular to a surface of the biological tissue is smaller than a dimension of the filament projected in a different plane.

6. The device of claim 5, wherein the incandescent lamp includes more than one filament.

7. The device of claim 5, further comprising:
   more than one incandescent lamp.

8. The device of claim 1, further comprising:
   a reflector having an inner surface facing the incandescent lamp, the reflector configured to receive reflected radiation from the biological tissue and return the reflected radiation to the biological tissue,
   wherein the waveguide is configured to direct radiation having a wavelength between about 600 nm and about 2500 nm between biological tissue and the reflector.

9. The device of claim 8, wherein the device is configured to nonselectively preheat biological tissue using radiation not reflected from the biological tissue.

10. The device of claim 8, wherein the waveguide comprises a spectral filter and a transparent dielectric.

11. The device of claim 10, wherein the spectral filter comprises a reflecting coating coupled to the transparent dielectric.

12. The device of claim 10, wherein the spectral filter includes a liquid filter for selectively absorbing an infrared component of the emission from the incandescent lamp.

13. The device of claim 10, wherein the spectral filter comprises a fluorescent converter, a nonfreezing coolant fluid, and an optical thermal insulator.

14. The device of claim 10, wherein each of the reflector and the transparent dielectric comprise two halves having a plane of symmetry, each half having an inner surface and an outer surface, each transparent dielectric half mounted proximate to the inner surface of a corresponding reflector half, the transparent dielectric halves configured to grasp biological tissue when the transparent dielectric halves tend toward a closed position, the incandescent lamp located proximate to the inner surfaces of the reflector halves and proximate to the outer surfaces of the transparent dielectric halves.

15. The device of claim 14, wherein the inner surfaces of the reflector halves substantially form an ellipsoid of revolution when the reflector halves are in a closed position, and the inner surfaces of the transparent dielectric halves substantially form a sphere when the transparent dielectric halves are in the closed position.

16. The device of claim 14, wherein the inner surfaces of the reflector halves substantially form an elliptical cylinder when the reflector halves are in a closed position, and the inner surfaces of the transparent dielectric halves substantially form a cylinder when the transparent dielectric halves are in the closed position.

17. The device of claim 14, wherein the inner surfaces of the reflector halves substantially form an elliptical cylinder when the reflector halves are in a closed position, and the inner surfaces of the transparent dielectric halves substantially form a right prism when the transparent dielectric halves are in the closed position.

18. The device of claim 8, wherein at least a portion of the inner surface of the reflector is configured substantially as a portion of the inner surface of a sphere or ellipsoid having a center of curvature that is substantially located on a facet of the waveguide.

19. The device of claim 18, wherein at least a portion of the inner surface of the reflector is configured substantially as an inclined surface rising from the facet of the waveguide.

20. The device of claim 1, further comprising:

a cooler configured to reduce the temperature of a surface of the biological tissue.

21. The device of claim 1, further comprising:

a pain threshold sensor configured to control the electromagnetic radiation emitted from the incandescent lamp.

22. The device of claim 1, further comprising:

a light interrupter electrically coupled to the incandescent lamp, the light interrupter controlled by a patient activated switch.

23. The device of claim 1, wherein the power supply includes a battery.

* * * * *